(12) United States Patent
Thompson

(10) Patent No.: US 9,687,644 B2
(45) Date of Patent: Jun. 27, 2017

(54) SOFT, FLEXIBLE CONNECTOR

(75) Inventor: Robin R. Thompson, Pleasant Prairie, WI (US)

(73) Assignee: Hollister Incorporated, Libertyville, IL (US)

( * ) Notice: Subject to any disclaimer, the term of this patent is extended or adjusted under 35 U.S.C. 154(b) by 442 days.

(21) Appl. No.: 13/819,585

(22) PCT Filed: Aug. 29, 2011

(86) PCT No.: PCT/US2011/049555
§ 371 (c)(1),
(2), (4) Date: Apr. 19, 2013

(87) PCT Pub. No.: WO2012/030721
PCT Pub. Date: Mar. 8, 2012

(65) Prior Publication Data
US 2013/0218112 A1    Aug. 22, 2013

Related U.S. Application Data

(60) Provisional application No. 61/379,476, filed on Sep. 2, 2010.

(51) Int. Cl.
| | | |
|---|---|---|
| *A61M 5/30* | (2006.01) |
| *A61M 39/10* | (2006.01) |
| *A61F 5/455* | (2006.01) |
| *A61M 37/00* | (2006.01) |
| *A61M 5/32* | (2006.01) |
| *A61B 19/00* | (2006.01) |
| *B67D 7/60* | (2010.01) |
| *B65D 5/72* | (2006.01) |
| *A61M 39/12* | (2006.01) |

(52) U.S. Cl.
CPC ............ *A61M 39/10* (2013.01); *A61F 5/455* (2013.01); *A61M 39/12* (2013.01)

(58) Field of Classification Search
CPC .......... A61M 5/30; A61M 37/00; A61M 5/32; B67D 7/60; B65D 5/72
See application file for complete search history.

(56) References Cited

U.S. PATENT DOCUMENTS

| | | |
|---|---|---|
| 4,603,890 A | 8/1986 | Huppee |
| 4,637,384 A | 1/1987 | Schroeder |
| 4,675,020 A | 6/1987 | McPhee |

(Continued)

FOREIGN PATENT DOCUMENTS

| | | | |
|---|---|---|---|
| GB | 2323418 A | * | 3/1997 |
| GB | 2323418 A | | 9/1998 |

OTHER PUBLICATIONS

International Search Report for PCT/US2011/049555 dated Jan. 27, 2012.

*Primary Examiner* — Tatyana Zalukaeva
*Assistant Examiner* — Ilya Treyger
(74) *Attorney, Agent, or Firm* — Levenfeld Pearlstein, LLC

(57) ABSTRACT

A soft, flexible fluid connector includes a connecting portion and a skirt formed integral therewith and depending therefrom. The skirt has formed spaces around the circumference of the skirt defining flexible, compressible, fingers. The connector is overmolded with a plastic or like flexible material wherein the formed spaces are filled with the flexible material such that the connector is molded contiguously with a flange or faceplate.

17 Claims, 3 Drawing Sheets

(56) References Cited

U.S. PATENT DOCUMENTS

| | | | |
|---|---|---|---|
| 4,951,391 A | | 8/1990 | Seabra |
| D333,178 S | | 2/1993 | Novy |
| 5,531,534 A | | 7/1996 | Urbach |
| D388,876 S | | 1/1998 | Sampson |
| 5,890,610 A | * | 4/1999 | Jansen .................. A61J 1/2089 215/253 |
| 5,909,902 A | | 6/1999 | Seabra |
| 6,003,906 A | | 12/1999 | Fogarty et al. |
| 6,113,583 A | * | 9/2000 | Fowles ..................... A61J 1/10 604/403 |
| D453,815 S | | 2/2002 | Hoenig |
| 6,419,281 B1 | | 7/2002 | Salomon-Bahls et al. |
| 7,743,799 B2 | * | 6/2010 | Mosler .................. A61J 1/2096 141/302 |
| 2002/0082586 A1 | | 6/2002 | Finley et al. |
| 2007/0112313 A1 | | 5/2007 | Fangrow |

\* cited by examiner

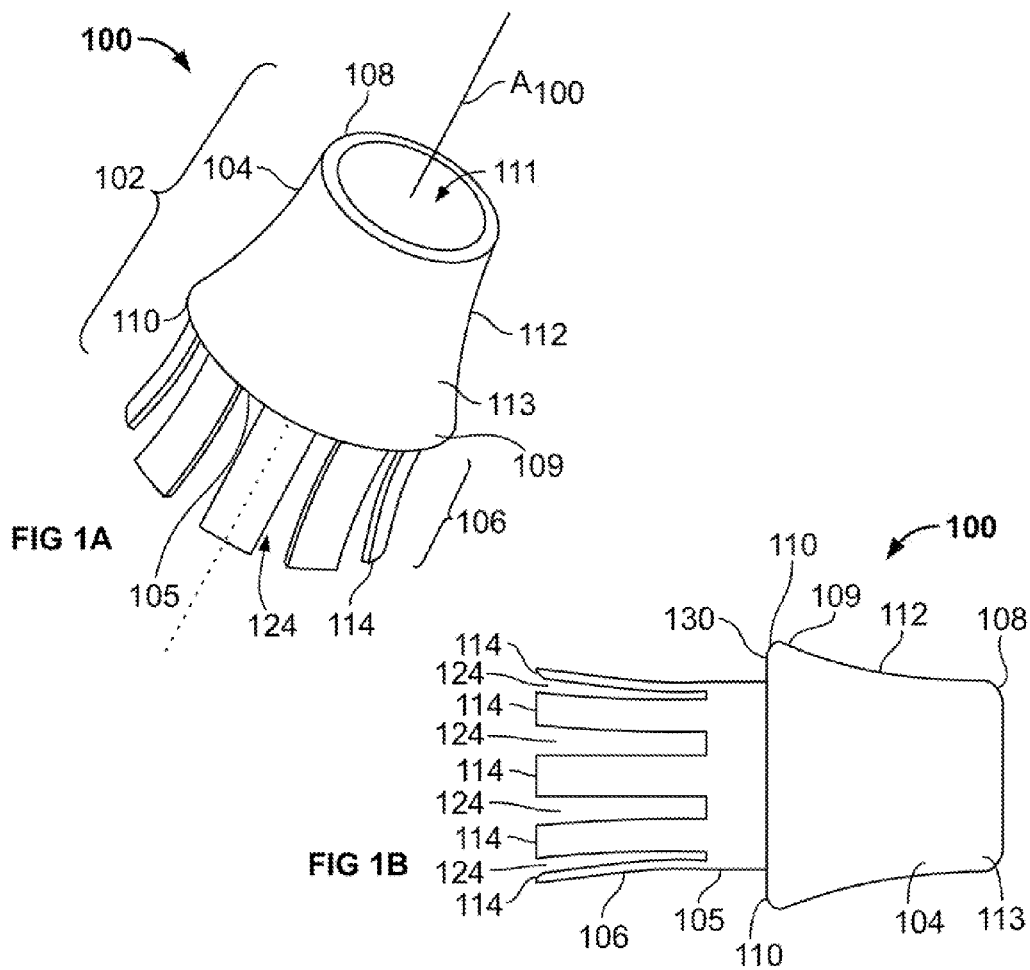
FIG 1A
FIG 1B
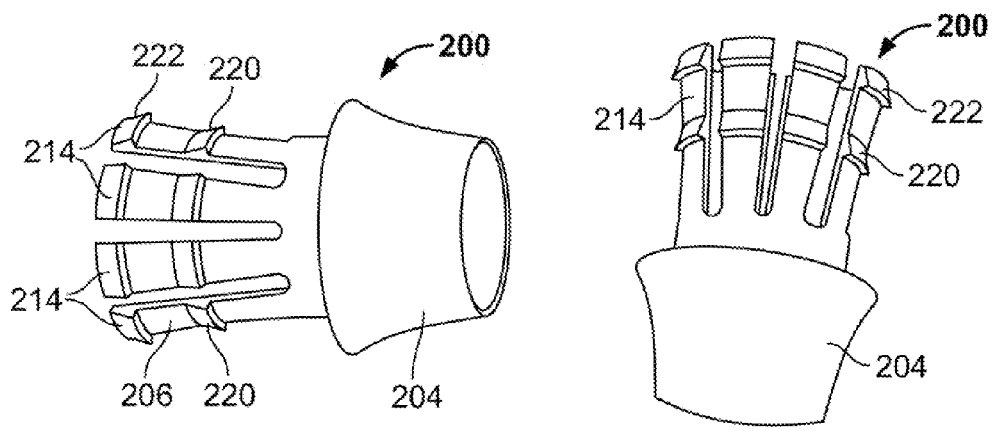
FIG 2A
FIG 2B

SOFT, FLEXIBLE CONNECTOR

CROSS-REFERENCE TO RELATED APPLICATION DATA

This application claims the benefit of priority of PCT/US2011/049555 filed Aug. 29, 2011, which claims the benefit of priority of U.S. Provisional Application No. 61/379,476 filed Sep. 2, 2010 entitled "SOFT, FLEXIBLE CONNECTOR."

BACKGROUND

The present disclosure is directed to a connector for connecting tubes and hoses to an associated device. More particularly, the present disclosure is directed to a soft, flexible connector.

Fluidic connectors are used in a wide variety of systems. Such connectors can be used, for example, in applications that require draining a fluid away from a body, such as a human body. Often such connectors are located, in close proximity to the body. In one such application, connectors are used in female external catheter ("FEC") systems, which generally include a form-fitting pouch, having a drainage connector, and an associated drainage tube. Typically, the pouch conforms to the shape of the female genitalia. The connector provides flow communication between the pouch and the drainage tube, and allows the tube to be disconnected from the pouch as desired. The drainage connection is typically made from hard, rigid plastic such that a flexible tube can be securely mounted to the connector to drain away fluid from the body and pouch into an associated bag or collection container.

The drainage connectors, while functional, are rigid and inflexible in order to provide a secure connection for the tubing, as well as to provide sufficient pull-out strength when the tube is removed and/or replaced. Unfortunately, when a new tube is mounted onto the connector, the hard plastic connector can come into contact with the user's skin and genitalia, causing discomfort to sensitive areas. Such discomfort can lead to the user changing drainage tubes less often than necessary or avoiding use of the appliance all together in order to avoid the discomfort.

Accordingly, there is a need for comfortable, flexible connector. Desirably, such a connector can be adapted for use with FEC systems. Such a connector is easily formed and does not decrease the strength of efficacy of the connection with an associated drainage tube. More desirably, such a connector has both strength in the longitudinal and axial directions, but provides a "soft" feel when longitudinally compressed. More desirably still, such a connector reduces discomfort to the user when disconnecting and/or reconnecting tubes, while enhancing pull-out strength.

BRIEF SUMMARY

A flexible fluid connector device includes a hollow body defined by a connecting portion and a skirt formed integral with one another. The skirt has formed spaces around the circumference at a lower portion thereof that define a plurality of flexible, compressible lingers. A collar portion at an upper portion of the skirt distinguishes the fingers from the connecting portion.

The connecting portion, can be formed as a cap, having a nozzle-shaped profile, having a top and a bottom, and an interior and an exterior. The interior of the cap is hollow, while the exterior of the cap has smooth, rigid sides sloping from the top to the bottom in a bell or mushroom-like configuration. The cap also has a lip or ledge at the bottom of the cap adjacent to the skirt. The connecting portion can also be formed with other types of mechanical connecting fittings, such as bayonet-type mounts, Luer-type fittings, screw or threaded fittings and the like.

The formed spaces in the skirt extend from, the collar to a free end of the skirt. The spaces may be symmetrically or asymmetrically positioned circumferentially around the skirt. Similarly, the fingers defined by the spaces may be symmetrically or asymmetrically positioned around the circumference of the skirt.

In one embodiment, the connector is overmolded such that the formed spaces are filled with a material and the connector is molded integrally with a flange for or faceplate for an associated appliance, such as the exemplary FEC device. Optionally, the connector can include friction-enhancing elements on each of the fingers. The present connector provides a pull-out strength greater than that of a connector having a skirt with no fingers, and greater comfort afforded to the patient.

These and other features and advantages of the present device will be apparent from the following detailed description, in conjunction with the appended claims.

BRIEF DESCRIPTION OF THE SEVERAL VIEWS OF THE DRAWINGS

The benefits and advantages of the present device will become more readily apparent to those of ordinary skill in the relevant art after reviewing the following detailed description and accompanying drawings and photographs, wherein:

FIGS. 1A and 1B are perspective views of an embodiment of a connector;

FIGS. 2A and 2B are various views of another embodiment of the connector;

DETAILED DESCRIPTION

Figure 3:
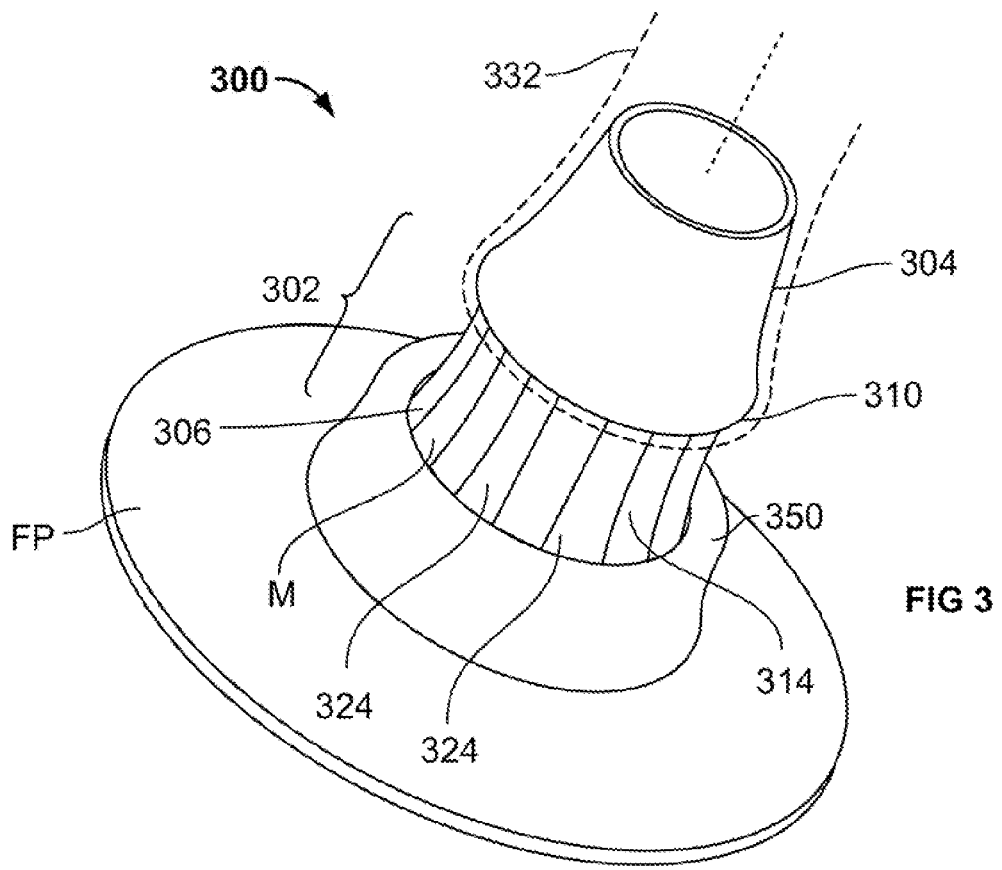
FIG. 3 is a perspective view of still another embodiment of the connector.

While the present disclosure is susceptible of embodiment in various forms, there is shown in the drawings and will hereinafter be described a presently preferred embodiment with the understanding that the present disclosure is to be considered an exemplification of the device and is not intended to limit the disclosure to the specific embodiment illustrated.

It should be further understood that the title of this section of this specification, namely, "Detailed Description", relates to a requirement of the United States Patent Office, and does not imply, nor should be inferred to limit the subject matter disclosed herein.

Figure 5:
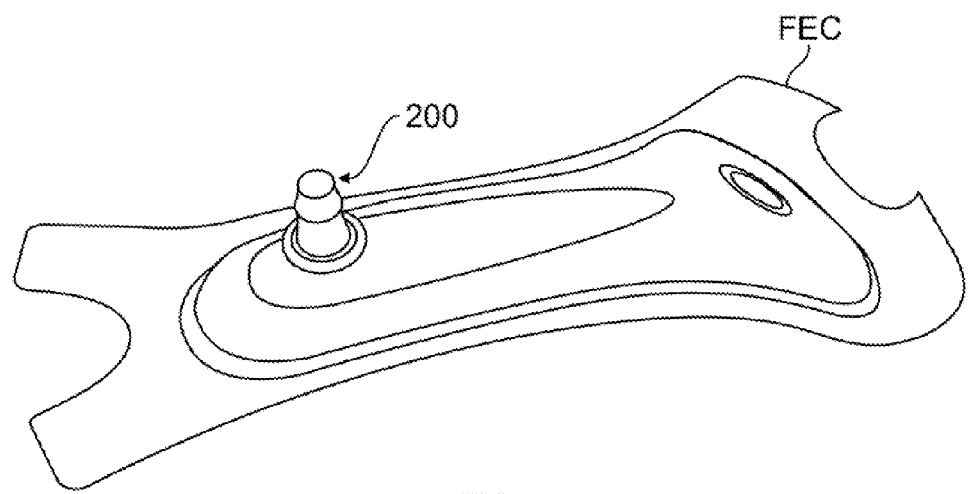
FIG. 5 is a perspective view of a female external catheter (FEC) with a soft flexible connector mounted thereto.
Figure 6:
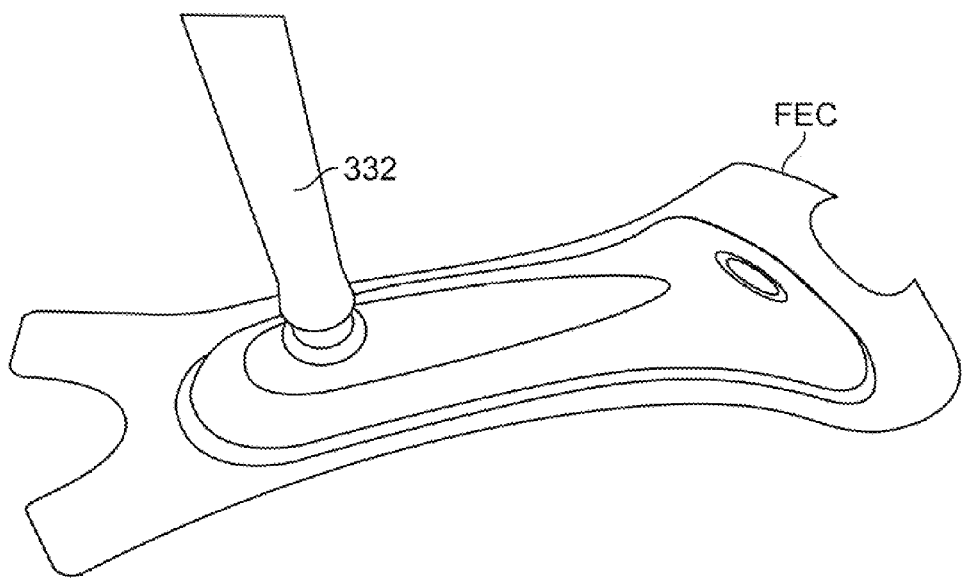
FIG. 6 is a perspective view of the FEC with a drainage tube mounted to the connector.

A soft, flexible connector for use with, for example, an FEC device, such as that illustrated in FIGS. 5 and 6, includes a hollow body defined by a cap, and a skirt having formed spaces around the circumference of the skirt defining flexible, compressible fingers. The connector may be overmolded with a plastic or like flexible material wherein the formed spaces are filled with a pliable, flexible material such that the connector is molded contiguous with a flange or a faceplate of the exemplary FEC device.

Referring now to the figures and in particular to FIGS. 1A and 1B, an embodiment of the soft, flexible connector 100 is shown. The connector 100 has a hollow, generally cylindrically-shaped body 102 with a central longitudinal axis $A_{100}$. The body 102 is defined by a connecting portion 104, such as the exemplary cap, and a skirt 106 depending from the cap 104. The cap 104 and skirt 106 are configured concentrically around the central longitudinal axis $A_{100}$. An upper portion of the skirt 106, adjacent the cap 104 defines a collar portion 105. Although a circular cross-sectional shape is depicted for the connector 100, it will be recognized that any suitable cross-sectional shape could be used (for example, oval, elliptical or irregularly shaped).

The cap 104, which essentially defines a barbed fitting, is tubular and nozzle-shaped, having a top edge 108 and a bottom 109 region, an interior 111 and an exterior 113. The interior 111 of the cap 104 is hollow. The exterior 113 of the cap 104 has smooth, rigid sides 112 which slope gradually outwardly from the top edge 108 to define a wider bottom region 109. The cap 104 has a generally bell or mushroom-shaped configuration. A lip 110 at the bottom region 109 of the cap 104 extends axially outwardly to overhang the skirt 106.

The collar 105 is adjacent to the lip 110 and is contiguous with the cap 104. The collar extends from an undersurface 130 of the lip 110 to fingers 114 and formed spaces 124 at a distal or free end of the skirt 106.

The fingers 114 are defined by a plurality of formed spaces 124 in the skirt 106. The spaces 124 extend from the collar 105 to the free end of the skirt 106. As illustrated, the spaces 124 can be formed with a roundness terminus at the juncture with the collar 105, and can be slightly flared at the distal ends, or at the free end of the skirt 106. The rounded terminus reduces stresses at the juncture with the collar 105. The spaces 124 can be positioned symmetrically or asymmetrically circumferentially around the skirt 106. There can be an even or an odd number of spaces 124. The spaces 124 can be uniform in size and shape or may differ in size and shape from one another.

The fingers 114 are defined by the spaces 124, and in the exemplary embodiment are symmetrically formed in the skirt 106. In the illustrated embodiment, eight fingers 114 are present; however, it will be appreciated by those with skill in the art that any odd or even number of fingers 114 can be formed in the skirt 106, and that such fingers 114 can be arranged in a number of different ways in keeping with the scope and spirit of the present disclosure.

FIGS. 2A and 2B illustrate another embodiment of the connector 200 having a cap 204 and a skirt 206. The skirt 206 has fingers 214 defined by formed spaces 224 between each of the fingers 214. The fingers 214 have friction-enhancing elements 220, 222 on an exterior surface of the fingers 214. Such friction-enhancing elements 220, 222 may be in the form of barbs, such, as the proximal and distal barbs 220, 222 illustrated in FIGS. 2A and 2B. The barbs 220, 222 can be formed symmetrically vis-à-vis the slope of the faces of the barbs relative to the fingers, or they can be formed with steeper side angles or slope facing the cap 204 to increase pull-out resistance once a tube is engaged with the connector 200. Such friction-enhancing elements 220, 222, can also include textured surfaces on the fingers 214, hooks, and the like.

Figure 4:
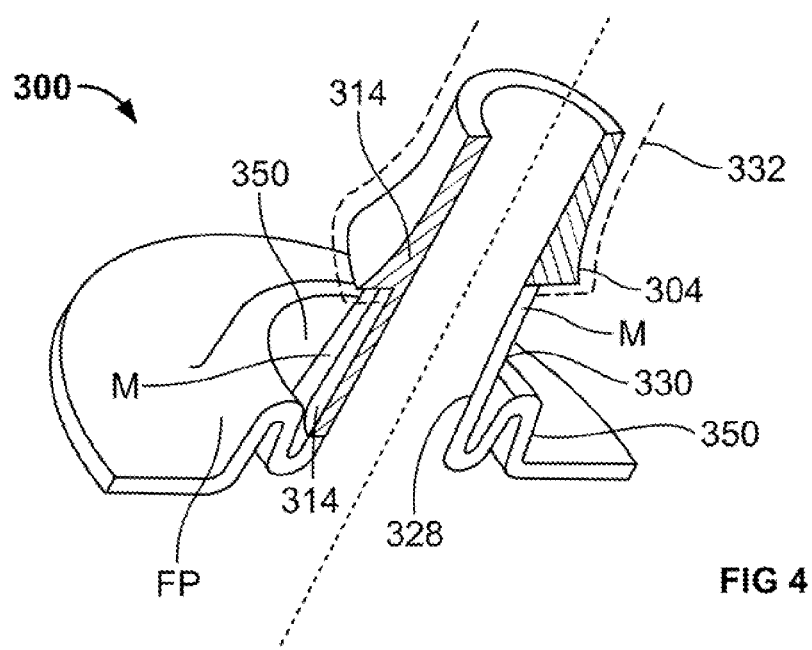
FIG. 4 is a longitudinal cross-section of the connector of FIG. 3.

Turning now to FIGS. 3 and 4, the connector 300 is overmolded or insert molded (collectively referred to as overmolded for ease of description) such that the spaces 324 are filled and are contiguous and continuous with a faceplate FP. The faceplate FP can be formed as a flange to provide for ease of mounting to, for example, the pouch. It will be appreciated by those skilled in the art that connector 300 represents both connector 300 or connector 200 or any combination of the two. In the illustrated example, only the region of the skirt 306 in which the fingers 314 are formed is overmolded, however, it is anticipated that portions of the body 302 of the connector 300 may also be overmolded.

In the connector 300, the formed spaces 324 are filled with a material M, such as a polymer, for example, a thermoplastic elastomer or like material that may or may not be the same material that forms the faceplate FP. It is anticipated that the connector 300 and overmolding material M will be different from one another to obtain different characteristics as desired. For example, it is contemplated that the connector 300 material will be stiffer and more rigid than the overmolding material. It is also anticipated that the overmolding material and the faceplate FP or flange will be formed as an integral unit in the overmolding process so that the faceplate FP or flange and connector 300 flow seamlessly and uninterruptedly into one another.

The skirt 306 of the connector 300 may be overmolded such that the fingers 314 have the same, greater, or lesser diameter as the diameter of the overmold 350. In such an arrangement, it is anticipated that the thickness of the fingers 314 will be about the same as the thickness of the overmold, such that the fingers 314 and overmold M are flush along both the inner and outer peripheries 328, 330, of the skirt 306. Alternately, it will be appreciated that finger and overmold thicknesses can be different and that the ringers 314 and overmold M can be flush along the inner or the outer peripheries, 328, 330, or that the fingers 314 can be fully encapsulated or enveloped by the overmold M.

The overmold material 350 can bond, or adhere, not simply to an outer or inner surface of the skirt 306, but also to the lateral sides of the fingers 314 as well. Thus, if the fingers 314 are positioned in the center of the overmold 350, the overmold 350 can surround each finger 314 individually and bond to an exterior surface, an interior surface, the bottom, and both lateral sides of each finger 314. It is believed that such bonding increases the pull-out force needed to disengage the connector 300 from the faceplate FP.

The connector 300 described above can be coupled or connected to a drainage device tube 332 (shown in phantom). The drainage device tube 332 can be coupled, to the cap 304 of the connector 300 such that the drainage device tube 332 is external to the exterior surface of the cap 304, and affixed over the lip 310. The drainage device tube 332 can be removed from the connector 300 by simply pulling the drainage device tube 332 from the connector 300. The connector 300 has increased pull-out strength as a result of the fingers 314 which is increased by the overmolding of the connector skirt 306, making the connector 300 less likely to separate from the faceplate FP on withdrawal of the drainage device tube 332.

The advantages to the present connector 100, 200, and 300 will be appreciated by those skilled in the art. The fingers 114, 214, and 314 are configured to flex and compress toward the central axis of the connector, add flexibility and softness to the FEC device, while maintaining the necessary rigidity for coupling tubes and the like. In addition, when the connector 100, 200, 300 is coupled to a hose, tube, or other fluid handling device, the fingers 114, 214, and 314, surprisingly, increase the pull-out strength of the connector from the faceplate FP, both when the connector is overmolded and when the connector is not overmolded. Increase in pull-out strength allows for fluid-handling devices to be removed and coupled repeatedly without the threat of the adapter 100, 200, 300 becoming disengaged or separated from the faceplate FP quickly and easily. Pull-out strength is also enhanced by the friction-enhancing elements, such as barbs which are used to fasten or couple the fingers 114, 214, 314 to the faceplate FP of the FEC in a non-overmolded embodiment.

It will be appreciated by those skilled in the art that although the present connecting portion 104 is disclosed and discussed in reference to a barbed fitting or cap, various other types of mechanical connections or fittings can be used with the present soft, flexible connector. For example, rather than a barbed end or cap disclosed, a bayonet-type fitting, a Luer-type fitting, a screw/threaded connection fitting and the like can be used.

It will also be understood by those skilled in the art that reference to fluid includes liquids, gases or a combination of liquids and gases and may also include fluids with entrained solid matter.

All patents referred to herein, are incorporated herein by reference, whether or not specifically done so within the text of this disclosure.

In the present disclosure, the words "a" or "an" are to be taken to include both the singular and the plural. Conversely, any reference to plural items shall, where appropriate, including the singular.

From the foregoing it will be observed that numerous modifications and variations can be effectuated without departing from the true spirit and scope of the novel concepts of the present disclosure. It is to be understood that no limitation with respect to the specific embodiments illustrated is intended or should be inferred. The disclosure is intended to cover by the appended claims all such modifications as fall within the scope of the claims.

What is claimed is:

1. A flexible connector for use with a device for draining a fluid away from a body, comprising:
    a hollow body defining a connecting portion and a skirt integral with and depending from the connecting portion, the skirt having a free end and having formed spaces around a circumference of the skirt, the formed spaces defining a plurality of flexible, compressible fingers, wherein the formed spaces and the fingers are alternately positioned about the circumference of the skirt, the fingers each having a fixed end at the connecting portion and a free end, opposite to the fixed end, corresponding to the free end of the skirt, and wherein the connecting portion and skirt are made from a same material; and
    an overmold material disposed on and adhered to the hollow body at about the skirt, wherein the formed spaces are filled with the overmold material such that overmold material extends between the fingers within the formed spaces and about the free ends of the fingers and the connector is molded contiguously and integrally with a flange or faceplate formed from the overmold material.

2. The connector of claim 1 wherein the connecting portion is formed as a cap having a nozzle-shape profile, having a top and a bottom, an interior and an exterior, the interior of the cap being hollow, the exterior of the cap having smooth, rigid sides sloping from the top to the bottom in a bell or mushroom type configuration, the cap having a lip at the bottom of the cap adjacent to the skirt.

3. The connector of claim 2 wherein the formed spaces of the skirt extend from the free end of the skirt to a collar portion of the skirt adjacent to the lip.

4. The connector of claim 1 wherein the formed spaces are symmetrically positioned around a circumference of the skirt.

5. The connector of claim 1 wherein the fingers of the skirt defined by the formed spaces are symmetrically formed in the skirt, around a circumference of the skirt.

6. The connector of claim 1 wherein the fingers include friction-enhancing elements.

7. The connector of claim 1 wherein the overmold material and the fingers have an equal thickness.

8. The connector of claim 1 wherein an outer periphery of the fingers and an outer periphery of the overmold material are flush with one another.

9. The connector of claim 1 wherein an inner periphery of the fingers and an inner periphery of the overmold material are flush with one another.

10. The connector of claim 1 wherein the overmold material envelopes the fingers.

11. The connector of claim 1 wherein the overmold material is a thermoplastic elastomer or silicone.

12. The connector of claim 1, wherein the connecting potion is formed as a bayonet-type fitting or a Luer-type fitting or a screw/threaded connection fitting.

13. The connector of claim 1, wherein the hollow body has a length and an internal through passage extending the length of the hollow body, wherein an inner radial surface of the hollow body defines the internal through passage and the overmold forms at least a portion of the inner radial surface.

14. A connector comprising a hollow body extending in a longitudinal direction and defining a connecting portion and a skirt integral with and depending from the connecting portion, the skirt having a free end and having formed open spaces around a circumference of the skirt, the formed open spaces defining a plurality of flexible, compressible fingers, wherein the open spaces are open at the free end of the skirt in the longitudinal direction, wherein an internal through passage extends in the longitudinal direction through the connecting portion and skirt such that the connector includes respective openings at opposite longitudinal ends, and the formed open spaces extend from the internal through passage in a radial direction through a thickness of the skirt, and further including an overmold material molded over the skirt, the overmold material filling the spaces between the fingers, the overmold material being more pliable than the connector.

15. The connector of claim 14 wherein the overmold material has a thickness that is equal to a thickness of the fingers.

16. The connector of claim 14 including a flange formed integral with the overmold material, the flange extending beyond an outer periphery of the fingers at a free end thereof.

17. A flexible connector for use with a device for draining a fluid away from a body, comprising:
    a hollow body defining a connecting portion and a skirt integral with and depending from the connecting portion, the skirt having a free end and having formed spaces around a circumference of the skirt, the formed spaces defining a plurality of flexible, compressible fingers, wherein the formed spaces and the fingers are alternately positioned about the circumference of the skirt, the fingers each having a fixed end at the connecting portion and a free end, opposite to the fixed end, corresponding to the free end of the skirt; and an overmold material disposed on the connector at about the skirt, wherein the formed spaces are filled with the overmold material such that overmold material extends between the fingers within the spaces, about the free ends, and over inner and outer radial surfaces of the fingers so as to envelope the fingers.

\* \* \* \* \*

UNITED STATES PATENT AND TRADEMARK OFFICE
CERTIFICATE OF CORRECTION

PATENT NO.        : 9,687,644 B2                     Page 1 of 1
APPLICATION NO.   : 13/819585
DATED             : June 27, 2017
INVENTOR(S)       : Robin R. Thompson It is certified that error appears in the above-identified patent and that said Letters Patent is hereby corrected as shown below:

In the Specification

Column 1, Line 21, "located," to read as --located--.

Column 1, Line 47, "of" to read as --or--.

Column 1, Line 61, "lingers." to read as --fingers.--.

Column 2, Line 7, "from," to read as --from--.

Column 3, Line 43, "embodiment" to read as --embodiment,--.

Column 3, Line 56, "such," to read as --such--.

Column 4, Line 31, "ringers" to read as --fingers--.

Column 4, Line 47, "coupled," to read as --coupled--.

Signed and Sealed this
Twelfth Day of December, 2017

Joseph Matal
*Performing the Functions and Duties of the*
*Under Secretary of Commerce for Intellectual Property and*
*Director of the United States Patent and Trademark Office*